United States Patent [19]

Wallach et al.

[11] Patent Number: 5,795,975
[45] Date of Patent: Aug. 18, 1998

[54] TNF RECEPTOR PROMOTER

[75] Inventors: David Wallach, Rehovot, Israel; Oliver Kemper, Bockenheim, Germany; Peter Kuhnert, Berne, Switzerland

[73] Assignee: Yeda Research and Development Co. Ltd., Rehovot, Israel

[21] Appl. No.: 532,309

[22] Filed: Sep. 22, 1995

Related U.S. Application Data

[63] Continuation-in-part of Ser. No. 178,564, Jan. 7, 1994, abandoned.

[30] Foreign Application Priority Data

Jan. 10, 1993 [IL] Israel .................................. 104355

[51] Int. Cl.⁶ ........................... C07H 21/04; C12N 15/00
[52] U.S. Cl. ...................... 536/24.1; 435/320.1; 935/6; 935/36
[58] Field of Search ........................ 536/24.1; 514/44; 435/320.1; 935/6, 36

[56] References Cited

FOREIGN PATENT DOCUMENTS 0 231 624   8/1987   European Pat. Off. .
0 417 563   3/1991   European Pat. Off. .
0 433 900   6/1991   European Pat. Off. .

OTHER PUBLICATIONS

Derre et al., "The gene for the type 1 tumor necrosis factor receptor (TNF–R1) is localized on band 12p13", Human Genetics, vol. 87, pp. 231–233 (1991).

Fuchs et al., "Structure of the human TNF receptor 1 (p60) gene (TNF1) and localization to chromosome 12p13" Genomics, vol. 13, pp. 219–224 (1992).

Kemper et al., "Cloning and partial characterization of the promoter for the human p55 tumor necrosis factor (TNF) receptor", Gene, vol. 134, pp. 209–216 (1993).

TA Brown, "Gene cloning: An Introduction", pp. 153–177 (1990).

LH Guo et al., "Nucleic Acids Research", pp. 5521–5540 (1983).

JP Watson et al., "Recombinant DNA", pp. 153–159 (1992).

A Bielinska et al., Science, vol. 250, pp. 997–1000 (1990).

N Miller et al (1994) Parasitology Today 10:92–97.

RA Stull et al (1995) Pharmaceutical Research 12: 465–483.

S Wu–Pong (1994) Pharmaceutical Technology 118: 102–114.

RW Wagner (1994) Nature 372: 333–335.

Y Rojanasakul (1996) Advanced Drug Delivery Reviews 18: 115–131.

*Primary Examiner*—Bruce R. Campell
*Attorney, Agent, or Firm*—Browdy and Neimark

[57] ABSTRACT

A DNA molecule containing the endogenous first intron-located p55 TNF-R gene promoter/enhancer sequence is provided. Also provided is a DNA molecule which contains a gene in operative association with a promoter sequence that includes the endogenous first intron-located p55 TNF-R gene promoter/enhancer sequence.

9 Claims, 3 Drawing Sheets

FIG. 3

```
          SacI              S1HS           SP-1
  1   GAGCTCACGGAATGGGTTTAGCTGTGTTGAACTGGAGGAGGAGCTGGGCGGGGCCTCAGCTAAAGGCCG
          SP-1?                                GC, early-seq1, HTLV-pA-BS.1
 81   CTGAGGGGCTAGGAGGAGCCAAGTGCCCTCAGGAAGGAGGGCACAGACCTGATGGGCGGAAGCAGGGTCGAGGGAGA
161   CTTCCCTTCGGATGGAATGGGAGAGGAGGCATTCCCGGAACATGTGGGCCAAGGTGGGACAAGGGTCTGTGGCCTGG
          Octamer                                                              Kr/bcd
241   CTCTTTGCATGGGAGGGGATGGGATGGGAGTGGGGGTTGAGTGGGGAAGGAGGGACTTGGCCATAGGAAGAAGGGATTAG
          octamer                            AP-1, heptamer
321   ATGGAGTCCCACTTGCATGCAGGCTGGTGCCTTCTGCCTTTCTGCTGACTCATGACCCTTGAGGAGCTGGGGAAGCTGCT
          JCV AvrII  JCV        AP-1     SP-1 (SV40)                          JCV
401   AGTTCCCTCCTCTCCCCTAGGTCTCCCCTCGGCCTGAGTCACTGGGGCGGAGTTGCTGGGAAAAGATTTCCCTCCCT
                                SV40.13                                          SP-1?
481   CCCGGATCTGACTTAACCCCCAGAGTGCTGGAAAGAGAAGGAACACGTGCCTGAGAAAGCCTCTCCCTCCCTCCCCT GGGGCGTCCCCA
561   CCAGGGAGGCTCATCCCCCACTGGCCAGAGTCCCTGAAAATGCTCCCCTTTAAGGCTGTGTCTGGGCGTCCCCCA
                                                                              NFkB
641   GTTCTTCATCATGACTCTGCCTCAAGCCCCTGGATTCAAAGTACCAGTGACCTTAGGTGCTCCAGTGGCTTCTT
721   CGGGGAAAGGAACCACACTTTCAGGACTGGAAGTCTTCCCTACACACCCAACCTTCCTGTTGCCTGGAAGCCCCAGTCCT
                                                                     PR-uteroglobin
801   GTTCTCAGCAGAGGTTGTTGCCTCTGAGCAGGGGAAGGTTGTTGTCCTCTGAGCAGGGCACACGCCTCC
881   ACCTGCGGGGCTGCTGTGTGTTTCTGTGTGGCTTCCCCGTTGCGGCTTGAGGCTTGAACTTCCGGGCCTGCACAG
          PstI
961   CTTACAGCTGCAG
```

TNF RECEPTOR PROMOTER

CROSS-REFERENCE TO RELATED APPLICATIONS

The present application is a continuation-in-part of U.S. Ser. No. 08/178,564 filed Jan. 7, 1994, abandoned the entire contents of which are hereby incorporated by reference.

FIELD OF THE INVENTION

The present invention relates to a promoter sequence in the first intron of the p55 tumor necrosis factor receptor (p55 TNF-R) gene, to its preparation and use.

BACKGROUND OF THE INVENTION

TNF is a multifunctional pro-inflammatory cytokine which affects a wide range of cellular functions. On the one hand, TNF is involved in the protection of the organism, but on the other hand, when over-produced, it can play a major pathogenic role in several diseases. TNF is known to be involved in inflammatory processes and to be a mediator of the damage to tissues in septic shock (1), graft-versus-host reactions (2) and in rheumatic diseases (3).

TNF exerts these effects by binding to two distinct cell surface receptors, which differ in size (about 55 and 75 kDa) and possess structurally dissimilar intracellular domains, suggesting that they signal differently (4–11). Almost all cells express TNF receptors (TNF-Rs), yet the amounts and relative proportions of the two receptors vary in different cell types. These variations are in part developmentally controlled; they are related to the phenotype of the cell and its state of differentiation, and in part can be induced transiently by cytokines and immune stimulatory components of pathogens (12–22). Studies of the function of the two TNF-Rs indicate that they have different yet interacting activities (23–28), and that their activity level may be correlated to the extent of their expression by the cell (29,30). These findings imply that the mechanisms which affect the amounts and relative proportion of the two TNF-Rs can have significant influence both on the nature and the extent of the cellular response to TNF and thus constitute important determinants of the physiological as well as pathological manifestations of the function of this cytokine.

In order to inhibit the deleterious effects of TNF, ways were sought which would interfere with the binding of TNF to its receptors. Thus, neutralizing antibodies to TNF were raised (EP 186,833). Another approach to the inhibition of the action of TNF was the provision of soluble TNF receptors which compete with the cell surface TNF-Rs for the binding of TNF (EP 308,378 and EP 398,327).

Since binding to its receptors is required for TNF in order to exert its action, if less or no cell surface receptors are expressed, it should be possible to decrease or inhibit the deleterious effects of TNF. By the same token, it may be desired in certain cases to augment the beneficial action of TNF and in such a case this could possibly be achieved by increasing the amount of cell surface receptors expressed.

Parent U.S. application Ser. No. 08/178,564, abandoned, discloses a promoter sequence located in the 5' upstream region of the p55 TNF-R gene; sequence motifs and motif regions contained in the 5' upstream promoter sequence; methods for preparing these motifs or motif regions; and the use thereof in the modulation of TNF function. However, a promoter or promoter/enhancer region within the first intron of the p55 TNF-R gene has so far not yet been described.

SUMMARY OF THE INVENTION

The present invention provides a promoter sequence of the human p55 TNF-R gene which is located in the first intron of the gene and is contained within a 973 bp sequence.

The invention, in a preferred embodiment provides the 1.7 kb PstI fragment of the full length genomic clone encoding the human p55 TNF-R, which fragment encompasses part of the 3' end of the first intron of the p55 TNF-R gene and includes the promoter/enhancer region of the first intron.

The invention also provides the 973 bp (SEQ ID NO:1) SacI-PstI fragment of the above 1.7 kb PstI fragment.

The invention further provides the approximately 0.6 kb AvrII-PstI fragment (nucleotides 418–973 of SEQ ID NO:1) of the above 1.7 kb PstI fragment or 973 bp SacI-PstI fragment.

A promoter sequence according to the present invention may be employed for diagnosing either inherited or acquired mutations in the promoter regions (the intron promoter regions) which contribute to the pathology of diseases. It can also be used in recombinant DNA technology as a promoter in combination with a nucleotide sequence encoding any given protein in the same manner that known promoters are presently used. The sequences of the present invention, and particularly the DH-site IIb, may act not only as a promoter or enhancer, but also as a tissue-specific element which might be useful for, e.g., expressing genes in transgenic mice that are toxic to B cells or for gene therapy if the expression of the introduced gene in B cells is undesirable.

While it is known that the 5' upstream promoter sequence is capable of controlling the expression of the native p55 TNF-R gene product (see USSN 08/178,564,abandoned), the first intron region promoter sequence of the present invention may control the expression of other forms (e.g. truncated forms) of the p55 TNF-R. Further, the first intron promoter appears to function as an enhancer element for the transcription of the p55 TNF-R gene, and hence this promoter sequence is also called a promoter/enhancer region.

The present invention therefore also provides other forms of the p55 TNF-R such as truncated forms expressed under the control of the first intron promoter.

In another aspect, the invention provides sequence motifs of transcription factor binding regions present in the above described promoter sequence. Such motifs have been shown to bind certain transcription factors which could be necessary for promoter activity and might be involved in regulation of this promoter.

The transcription factor-binding motifs may be prepared by deletion of the unwanted sequences upstream and/or downstream of the desired motif in the full sequence, i.e., by employing restriction enzymes to cut the full promoter sequence to arrive at the desired motif, and the resulting transcription factor-binding motif can then be inserted into a vector together with suitable control sequences and other conventional means required in order to obtain a vector which, on insertion into a suitable prokaryotic strain, is capable of expression of the desired transcription factor-binding motif on culturing of the strain.

The transcription factor-binding motif thus obtained can be used to screen, e.g., a human genomic library or a cDNA library for factors, e.g., transcription factors, binding thereto. Once these factors have been isolated, purified and identified by any conventional means, their inhibition should inhibit TNF-R formation, while their increased production should cause enhanced TNF-R expression, thereby leading to the desired effect of modulating TNF function, i.e., inhibition or enhancement of TNF binding to its receptors. While such motifs are denominated as "transcription factor-binding motifs" herein, it should be understood that such motifs may be found to bind to a factor which may not technically be a transcription factor. The terminology is intended to include motifs which bind any such factor which may be found by the screening disclosed herein.

Since the amount of specific transcription factors present in vivo is not unlimited, inhibition of TNF-R expression and consequent inhibition of deleterious TNF effects could also be achieved by the expression of a large number of transcription factor-binding motifs or motif regions. These will compete with promoters containing such transcription factor-binding motifs or motif regions for binding of the transcription factors. A "motif region" comprises the motif itself together with sequences flanking it on both sides, or several motifs connected by parts of the whole promoter sequence and flanked on both sides by sequence parts.

The present invention also provides pharmaceutical compositions comprising a transcription factor binding sequence motif according to the invention.

In another aspect, the invention provides pharmaceutical compositions comprising a transcription factor binding motif region according to the invention.

DESCRIPTION OF THE DRAWINGS

FIG. 3 shows schematically the nucleotide sequence of the 973 bp SacI-PstI fragment (SEQ ID NO:1) containing the DH-sites IIa and IIb of the first intron of the p55 TNF-R gene which has promoter and enhancer activity; the sites of the restriction endonucleases SacI, AvrII and PstI; the DH-sites IIa and IIb (in italics); and the transcription factor-binding motifs (underlined), are all shown as described in Example 1.

DETAILED DESCRIPTION OF THE INVENTION

Figure 1:
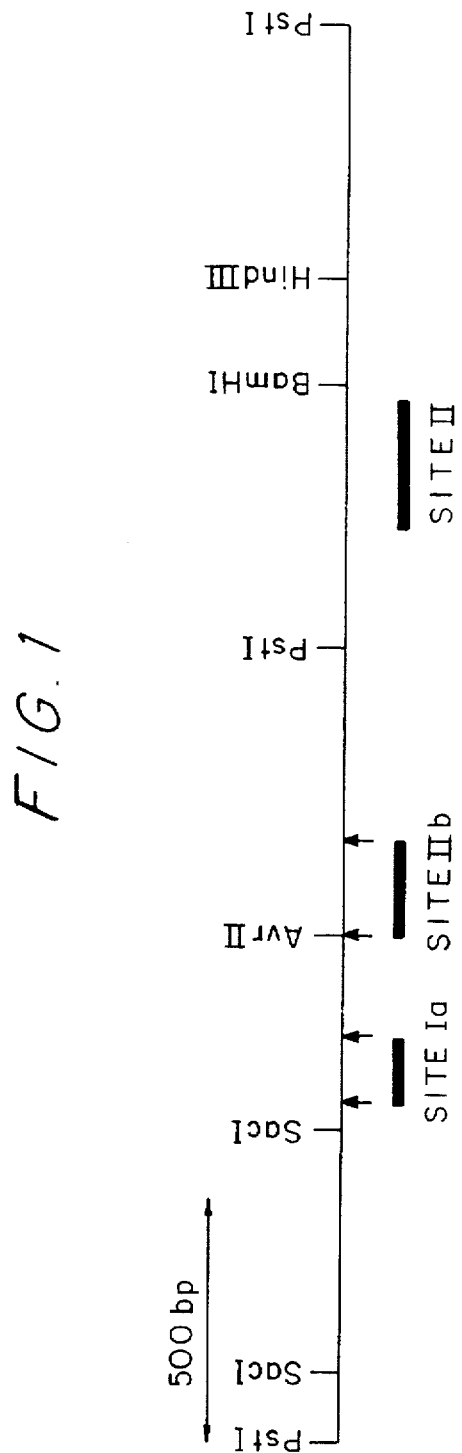
FIG. 1 shows schematically, the high-resolution mapping of DNase hypersensitive (DH)-sites in the first intron of the p55 TNF-R gene, in which are shown the DH-sites IIa, IIb and III (filled blocks) below a 3.1 kb fragment containing the 3' end of the first intron of the gene; and the various restriction endonuclease sites above this 3.1 kb fragment, as described in Example 1.

Using the full length genomic clone of the p55 TNF-R gene (see description thereof in U.S. Ser. No. 08/178,564, abandoned), it was found (see Example 1) by employing procedures of DNaseI hypersensitive site analysis and cloning of regions suspected to have promoter/enhancer activity, that a promoter/enhancer element exists in the 3' region of the first intron of the p55 TNF-R gene. The promoter/enhancer element was isolated and sequenced. Further, there was found a correlation between the presence of one of the DH-sites (DH-site II, which includes sites IIa and IIb) in the genomic DNA from various cell lines and the expression of p55 TNF-R mRNA. For example, in some B cell lines, where the DH-site II was absent or weak, it was also found that p55 TNF-R mRNA could not be detected, indicating that the promoter/enhancer element in which the DH-site II is present, is involved in transcriptional regulation of the p55 TNF-R gene. Moreover, cells which have high levels of p55 TNF-R mRNA expression, such as 293 cells, that were transfected with constructs containing the first intron promoter/enhancer element that included the DH-site IIb or containing both the DH-sites IIa and IIb (but not the DH-site IIa on its own), showed promoter and enhancer activity for these constructs, while certain B cell lines lacking p55 TNF-R mRNA expression that were transfected with the same constructs showed no enhancer activity for these constructs. Thus, it appears that the promoter/enhancer element of the first intron of the p55 TNF-R gene is active in a tissue-specific manner and its activity correlates with the state of differentiation of various cell types (e.g., BlastI and BlastII stages of various B cells as compared to different cell types such as HeLa, U937, 293, etc.).

The essential promoter/enhancer activity of the first intron region could be localized in an approx. 0.6 kb AvrII-PstI fragment which contains only the DH-site IIb. The larger fragments, inclusive of this AvrII-PstI fragment, such as a 1.7 kb PstI and a 973 bp. SacI-PstI fragment (all from a 3.1 kb fragment containing the 3' end of the first intron of the p55 TNF-R gene) had similar promoter/enhancer activities and tissue-specific activities.

The sequence analysis of the first intron promoter/enhancer region revealed that it contains several sites for B-cell specific transcription factors (such as octamer and heptamer sites), as well as known transcription factor binding sites.

Thus, in view of the above, it seems that the 5' upstream promoter region (disclosed in U.S. Ser. No. 08/178,564, abandoned,) of the p55 TNF-R gene is the region necessary for the promoter activity of the p55 TNF-R gene, in order to control the expression of the gene to ultimately result in the production of the normal p55 TNF-R. The presence of the promoter region in the first intron, according to the present invention, is indicative that the p55 TNF-R gene may encode other forms of the p55 TNF-R. Moreover, this promoter region in the first intron seems to function as an enhancer element for the transcription of the p55 TNF-R gene, this activity being apparently tissue-specific.

A number of putative motifs are discernable in the first intron promoter region of the invention (see FIG. 3) and include a S1HS motif of sequence GGAGGAGGA (nucleotides 44–52 of SEQ ID NO:1); SP-1 motifs of sequence GGGGCGGGGC (nucleotides 56–65 of SEQ ID NO:1) and GGGCGGAG (nucleotides 450–457 of SEQ ID NO:1), as well as SP-1 like motifs of sequences GGGGCTAGG (nucleotides 85–93 of SEQ ID NO:1) and GGGGCTGGG (nucleotides 623–631 of SEQ ID NO:1); a motif called G-C, early-seq1 or HTLV-pA-BS.1 (on the basis of its origin when discovered) of sequence GGGCG-GAAGCAGGGT (nucleotides 137–151 of SEQ ID NO:1); an octamer motif of sequences CTTTGCAT (nucleotides 243–250 of SEQ ID NO:1) and CTTGCAT (nucleotides 332–338 of SEQ ID NO:1); a Kr/bcd motif of sequence GAAGGGATTAG (nucleotides 310–320 of SEQ ID NO:1); and AP-1, heptamer motif of sequence CTGACTCATGA (nucleotides 365–375 of SEQ ID NO:1), and AP-1 motif of sequence CTGAGTCAC (nucleotides 439–447 of SEQ ID NO:1); a JVC motif of sequences CCCCTCCC, TCCCTCCC and TCCCTCCCTCCC (nucleotides 411–418, 425–432 and 548–559, respectively, of SEQ ID NO:1); an SV40.13 motif of sequence TGGAAAG (nucleotides 509–515 of SEQ ID NO:1); an NFkB motif of sequence GGAAGCCCC (nucleotides 786–794 of SEQ ID NO:1); and a PR-uteroglobin motif of sequence TGTCCTCT (nucleotides 853–860 of SEQ ID NO:1). These motifs are involved in, for example, the response to transcriptional factors which are affected by inducing agents, e.g., AP-2 and NF-kB. Further, these motifs may also allow for induced transient changes, superimposed on the pattern of constitutive expression of the receptor, perhaps by effects of certain cytokines which are formed at sites of inflammation. Moreover, as mentioned hereinabove and is set forth hereinbelow, these motifs may also be involved in the observed tissue-specific activity of the enhancer element of the intron promoter region, this enhancer element functioning as an enhancer for the transcription of the p55 TNF-R gene from its 5' upstream promoter region. The term "transcription factor binding motif" as used in the present claims is specifically defined as excluding the particular known motifs identified in this paragraph.

The present invention also concerns pharmaceutical compositions comprising a pharmaceutically acceptable carrier and a transcription factor-binding sequence motif or motif region of the present invention. These compositions may be used for treatment of any disease caused by an excess of TNF, either endogenously present or exogenously administered. Examples of diseases are septic shock, graft-versus-host reactions, rheumatic diseases and other autoimmune diseases. No claim is made herein that these diseases or conditions may be cured by means of the present invention. However, the deleterious effects of TNF which are involved in these diseases or conditions can be ameliorated by means of the present invention.

The way of administration can be via any of the accepted modes of administration for similar agents and will depend on the condition to be treated, e.g., intravenously, intramuscularly, subcutaneously, by local injection or by topical application, as the case may require.

The pharmaceutical compositions of the invention are prepared for administration by mixing the transcription factor-binding sequence motif or motif region with physiologically acceptable carriers, stabilizers and excipients, and prepared in dosage form, e.g., by lyophilization in dosage vials. The amount of active compound to be administered will depend on the route of administration, the disease to be treated and the condition of the patient. Local injection, for instance, will require a lower amount on a body weight basis than will, e.g., intravenous infusion.

Moreover, the pharmaceutical compositions of the present invention are those designed for the introduction of the active ingredients, namely, the transcription factor-binding motif sequences, into the target cells of choice, i.e., those expressing the p55 TNF-R, the expression of which it is desired to control via control of its promoter, which control may be either an enhancement or an inhibition of the promoter activity. To introduce such transcription factor-binding motif sequences into cells, a number of procedures are known, for example:

(i) It is possible to construct by standard procedures a recombinant animal virus vector (e.g., derived from vaccinia) to whose DNA two genes will be introduced, one encoding a ligand that binds to cell-surface proteins expressed specifically by the target cells (e.g., in the case of CD4 lymphocytes and related leukemias, the AIDS gp120 protein binds specifically to these cells), and hence expression of this gene will target the virus specifically to the desired cells; and the second encoding the transcription factor-binding motif sequence, which will be introduced and subsequently expressed in these cells, via the virus.

(ii) It is possible to prepare an oligonucleotide sequence encoding the transcription factor-binding motif sequence which can be introduced to the cells in the form of an ointment (e.g., as is used for wart treatment where an oligonucleotide sequence is introduced into skin cells using an ointment formulation, which oligonucleotide blocks the wart-inducing agent, a papillovirus). It is possible to introduce the above oligonucleotide sequence into the cells using the above recombinant animal virus in which the second sequence carried by this virus will be the oligonucleotide sequence.

(iii) It is possible to employ the recently developed ribozyme approach. Ribozymes are catalytic RNA molecules that specifically cleave mRNAs. Ribozymes may be engineered to cleave target RNAs of choice, e.g., the transcription factor-binding motif sequences of the invention. Such ribozymes would have a sequence specific for the transcription factor-binding motif sequence of choice and would be capable of interacting therewith (complementary binding) followed by cleavage of the transcription factor-binding motif sequence, resulting in a decrease (or complete loss) in the expression of the transcription factor-binding motif sequence it is desired to inhibit, the level of decreased expression being dependent upon the level of ribozyme expression in the target cell. To introduce ribozymes, in the form of a pharmaceutical composition, into the cells of choice (e.g., those carrying the p55 TNF-R), any suitable vector may be used, e.g., plasmid, animal virus (retrovirus) vectors, that are usually used for this purpose (see also (i) above, where the virus has, as second sequence, a cDNA encoding the ribozyme sequence of choice). Moreover, ribozymes can be constructed which have multiple targets (multi-target ribozymes) that can be used, for example, to inhibit the expression of one or more of the transcription factor-binding sequence motifs of the invention (for reviews, methods, etc., concerning ribozymes see 58–66).

Thus, the pharmaceutical compositions may be those comprising as active ingredient the above noted recombinant animal virus, or they may be an ointment comprising an oligonucleotide encoding the transcription factor-binding motif sequence. The amount of active compound to be administered will depend on the route of administration, the disease to be treated and the condition of the patient.

The invention is illustrated by the following non-limiting examples:

General Procedures and Materials
(a) Cell Lines and Culture Conditions

The human HeLa (31), Alexander, 293, SV-80 and mouse A932 cell lines were grown in Dulbecco's modified Eagle's medium. The human histiocytic cell line U937 (33) was grown in RPMI 1640 medium. Both media were supplemented with 10% fetal calf serum, 100 units/ml penicillin and 100 g/ml streptomycin. The human cell lines CEM, KM-3, Nahn-6, Daudi, Raji, Ramos, Ramos-B, Bjab, Bjab-B, P3HRI, ARH-77, were grown in RPMI 1640 medium supplemented with 20% FCS, 40 µg/ml gentamycin and 2 mU glutamine. The cell cultures were maintained in a 5% $CO_2$ atmosphere at 37° C.

(b) Cloning and Sequencing

The cloning and several features of the full-length genomic clone encoding the p55 TNF-R gene have been described (34). Further, as mentioned in U.S. Ser. No. 08/178,564, abandoned, and included herein as a reference for cloning procedures in general, a 1.16 kb NheI-PstI fragment of the above full-length genomic clone of the p55 TNF-R gene, comprising part of the first intron of the p55 TNF-R gene, the first exon, 5' flanking gene sequences and 180 bp of the left arm of the lambda phage, was subcloned into the pBluescript vector digested with XbaI and PstI. Partial deletions of this construct were made using the internal restriction sites EcoRI and BglII and various other standard cloning agents such as Klenow polymerase, ligase, etc., under standard conditions and procedures. Using these deletion constructs the promoter fragments were then excised from pBluescript with SacI and SalI and cloned into the CAT expression vector PGEMCAT (a generous gift from Dr. J. Chebath (35)) digested with SacI and SalI. DNA sequencing was performed using the chain termination method (36). These above constructs were sequenced using the T3 and T7 primers of pBluescript. Additional sequence information was obtained from within the cloned sequence using the oligonucleotide primers 5' CAATTCAGAATGCT-TAGCTTT (SEQ ID NO:2) and 5' GATCAGTAAATTC-CCAAGAAAGA (SEQ ID NO:3). The latter oligonucleotide was also used in a PCR reaction together with the T3 primer of the pBluescript vector to generate promoter fragments which are not linked to lambda phage sequences.

(c) Promoter Activity of a 5' Sequence in the p55 TNF-R Gene

To determine promoter activity of isolated DNA segments, the following procedure is set forth in U.S. Ser. No 08/178,564, abandoned, and is incorporated herein as a reference for analyzing promoter activity of DNA segments in general.

A full-length genomic clone of the p55 TNF-R was isolated from a human genomic library, using a partial cDNA clone of the receptor as a probe (34). Sequence analysis of the 5' end of the clone showed that it extends 810 nucleotides upstream of the translation start site of the protein. Unlike the coding region (38), the 5' extending region seemed to be devoid of disruption by introns.

To determine whether the cloned sequence has promoter activity, a fragment extending from an NheI site within the left arm of the lambda phage to a PstI site at pos. +168 within the gene sequence, and parts of this fragment, were cloned into pBluescript. The sequence from the translation start codon ATG upstream (bp−809 to −1) was subcloned using PCR technique, and this sequence, as well as deletions thereof, were examined for expression of CAT activity by a transient transfection assay. It was found that the full length fragment P1 drove effective expression of the CAT gene in human HeLa cells.

Deletion of 207 bp from the 3' end of the fragment P1 (P1) somewhat enhanced CAT expression. Deletion of only 74 bp from the 3' end of P1, led to decreased CAT expression. A significant increase was observed when 425 bp of the 5' end of P1 were deleted, suggesting the presence of a negative regulatory element in the deleted region. An even higher promoter activity was observed in deletion of both 5' 425 bp and 3' 207 bp sequences from P1.

Further deletion analysis revealed that the boundaries of the core promoter are between bp−355 to bp−287.

(d) Transient Transfection and CAT Assay

HeLa and A9 cells were seeded into 9 cm dishes (500,000 cells/dish) and allowed to grow for 16 h. CaPO$_4$-precipitates of DNA (37) were added to the medium and left on the cells for 12 h. The cells were then rinsed and allowed to grow in fresh medium for 48 h., rinsed again and scraped from the plates. Extracts were prepared and the CAT assay performed as described (37), using 20–25 g protein per sample. Incubation times ranged between 4–12 h. Each assay was done at least twice, with duplicate transfections for each construct tested.

Example 1

The Promoter and Enhancer Present in the First Intron of the p55 TNF-R Gene (i) Analysis of DNaseI-hypersensitive sites (DH-sites) in the p55 TNF-R gene In order to be able to store huge amounts of genetic information in a minimal space and to avoid unacceptable high viscosity resulting from large amounts of free DNA in the nuclei, genomic DNA has to be highly condensed. This is achieved by a very large number of unspecific DNA-binding proteins, the best characterized of which are the histone proteins encoded by the histone gene family. However, the tight packing and the covering of the DNA molecule with proteins is incompatible with transcriptional activity, for evidence has been accumulated that actively transcribed genes are less tightly packed especially in their 5' ends, that is, in their promoter regions. In addition, it has been shown that sites which bear regulatory elements which are distant from promoters are also accompanied by an "open" DNA structure, and that the occurrence of these structures is regulated together with the activation state of the regulatory element (42). Such "open" DNA structures can be detected rather simply by digesting isolated nuclei with nucleases, e.g., DNaseI, which will cut first those regions in the DNA which are not covered by proteins. In order to define the location of these sites on the gene, the probe used for hybridization must hybridize only to one end of the restriction fragment (indirect end labeling procedure (43)). The occurrence of DNaseI-hypersensitive sites (DH-sites) is generally associated with transcriptional regulation (44,45); however, it is conceivable that also other interactions which involve genomic DNA, such as replication, will require an open DNA state.

Accordingly, in accordance with the present invention, the first intron of the p55 TNF-R gene was analyzed for the presence of such regulatory elements such as promoters or enhancers by employing the procedure of DNaseI digestion of the p55 TNF-R gene to identify the DH-sites.

In U937 cells, which express high amounts of p55 mRNA, screening of the whole 16 kb p55 TNF-R gene revealed the presence of several DH-sites. The U937 cell line as well as many others (see below), were analyzed for DH-sites by standard procedures. Briefly, these procedures are as follows: the nuclei of the cells were extracted, isolated and subjected to DNaseI digestion. This was followed by extraction of the genomic DNA and subjection of the genomic DNA to digestion with various restriction endonucleases, for example, BglI, HindIII, BamHI and others. The so-digested genomic DNA was then Southern blotted and probed with various probes specific for the 5' upstream region (promoter) and for the first intron region of the p55 TNF-R gene.

Thus, in this way, DH-site I was detected either by digestion of the genomic DNA with PstI, followed by Southern blotting and probing with a 0.4 kb EcoRI-PstI fragment of the 5' upstream region of the p55-TNF-R (which fragment extends between nucleotides 600–978 of the sequence in Kemper and Wallach (46)); or digestion of the genomic DNA with HindIII, followed by Southern blotting and probing with a 0.6 kb PstI-BamHI fragment from the first intron and which includes the DH-site III (see FIG. 1). DH-sites II and III were detected either by digestion of the genomic DNA with BglI, followed by Southern blotting and probing with the 0.8 kb HindIII-PstI fragment which includes the 3' end of the first intron and extends into the second exon of the p55 TNF-R gene; or by digestion with HindIII or BamHI, followed by Southern blotting and probing with the 0.6 kb PstI-BamHI fragment which includes site III (See FIG. 1).

The results of the above analysis indicated that site I is located in the 5' upstream promoter, while the other sites are clustered in the first intron. The region of the intronic DH-sites contains two clusters, sites II and III, in most cell lines (see Table 1). High-resolution analysis of these clusters showed that cluster II consists of two separate DH-sites, IIa and IIb, while cluster III could not be resolved further. The precise location of these sites is shown in FIG. 1, which is a schematic representation of a 3.1 kb fragment at the 3' end of the first intron of the p55 TNF-R gene. The various restriction endonuclease sites are shown above the 3.1 kb fragment and the DH-sites IIa, IIb and III are depicted by filled blocks below the 3.1 kb fragment The p55 TNF-R gene is generally viewed as a housekeeping-gene, with low expression in most analyzed cell lines and tissues. The only exception to that are some B cell lines, which lack p55 TNF-R mRNA. We therefore also analyzed the pattern of intronic DH-sites in B cell lines of different differentiation states. We also analyzed the p55 TNF-R mRNA expression in these cell lines by standard Northern blotting procedures (46). The results are summarized in Table 1.

TABLE 1

DH-sites and p55 mRNA expression in various cell lines

| Cell Line | DH-site II | DH-site III | DH-site I | mRNA Northern |
|---|---|---|---|---|
| HeLa | ++ | ++ | + | +++ |
| U937 | ++ | ++ | + | +++ |
| CEM | ++ | ++ | n.d. | ++ |
| KM-3 | + | + | n.d. | + |
| Nalm-6 | + | + | n.d. | + |
| Daudi | (−) | + | n.d. | + |
| Ramos | (−) | + | n. d. | + |
| Ramos-B | − | + | n.d. | (−) |
| Raji | − | + | + | − |
| Bjab | − | + | + | − |
| Bjab-B | − | + | n.d. | − |
| P3HR1 | (−) | + | n.d. | n.d. |
| ARH-77 | (+) | + | n.d. | (+) |
| Alexander | ++ | + | n.d. | ++ |
| Hep-G2 | ++ | + | n.d. | + |
| 293 | ++ | + | n.d. | |
| SV-80 | ++ | + | n.d. | |

The symbols used in Table 1 above have the following meanings:
+++ = very high occurrence of DH-site or very high expression of mRNA
++ = high occurrence of DH-site or high expression of mRNA
+ = low occurrence of DH-site or low expression of mRNA
(−) = no detectable DH-site or no detectable expression of mRNA
n.d. = not done The indicated cell lines in Table 1 above were analyzed for DH-sites and for p55-TNF-R mRNA expression as detailed hereinabove.

From the results shown in Table 1 above it is apparent that DH-site III occurs in all cell lines, while site II is absent or very weak in B cells of the BlastI (Daudi, Raji, Ramos) and Blast II (Bjab) stage, and weak in finally differentiated cells (ARH-77). Similarly, p55 mRNA can be detected in all stages except for Blast I and Blast II stages. Interestingly, some BlastI lines express p55 TNF-R mRNA (Daudi and Ramos), but show a very weak DH-site II. These results demonstrate that the DH-site II is involved in transcriptional regulation of the p55 TNF-R gene, although it is not the only mechanism of regulation, since expression of p55 TNF-R mRNA is also possible in some cell lines that show a very weak DH-site II, as noted above.

(ii) Investigation of Promoter and Enhancer Activity of DR-site II Present in the First Intron of the p55 TNF-R Gene The fact that the appearance of a DH-site II is correlated with p55 TNF-R mRNA expression as noted in (i) above, suggested that this DH-site acts as an enhancer on the 5' upstream promoter of the p55-TNF-R gene. In order to test this possibility, we subcloned fragments containing DH-site II and linked them to the 5' upstream promoter of the p55-TNF-R gene and tested these constructs by transient transfection in 293 cells. The fragments were also investigated in a promoter-less vector in order to find out if they had promoter activity by themselves.

This was carried out by standard procedures: Briefly, a number of fragments containing the DH-sites, sites IIa, IIb and III, were sub-cloned into the luciferase expression vector pGL2 basic (Promega) for testing promoter activity in these fragments. This embodiment was intended to test for the promoter activity of the respective sites. The DH-site fragments were cloned at the 5' end of the luciferase expression vector as the sole promoter. Expression of luciferase would thus confirm promoter activity.

These fragments were also subcloned, at the 3' end of the luciferase gene, into the expression vector luc1, which contains the BglII-EcoRI fragment of the 5' upstream p55 TNF-R promoter (see (c) above, as well as Kemper and Wallach (46)) situated directly in front (5' end) of the luciferase gene, in order to test for enhancer activity in these fragments. By using the 5' upstream p55 TNF-R promoter, which has already been shown to have promoter activity, at the 5' end of the luciferase gene and the DH-site of the present invention at the 3' end of the same expression vector, the enhancer activity of these fragments could be determined.

Figure 2:
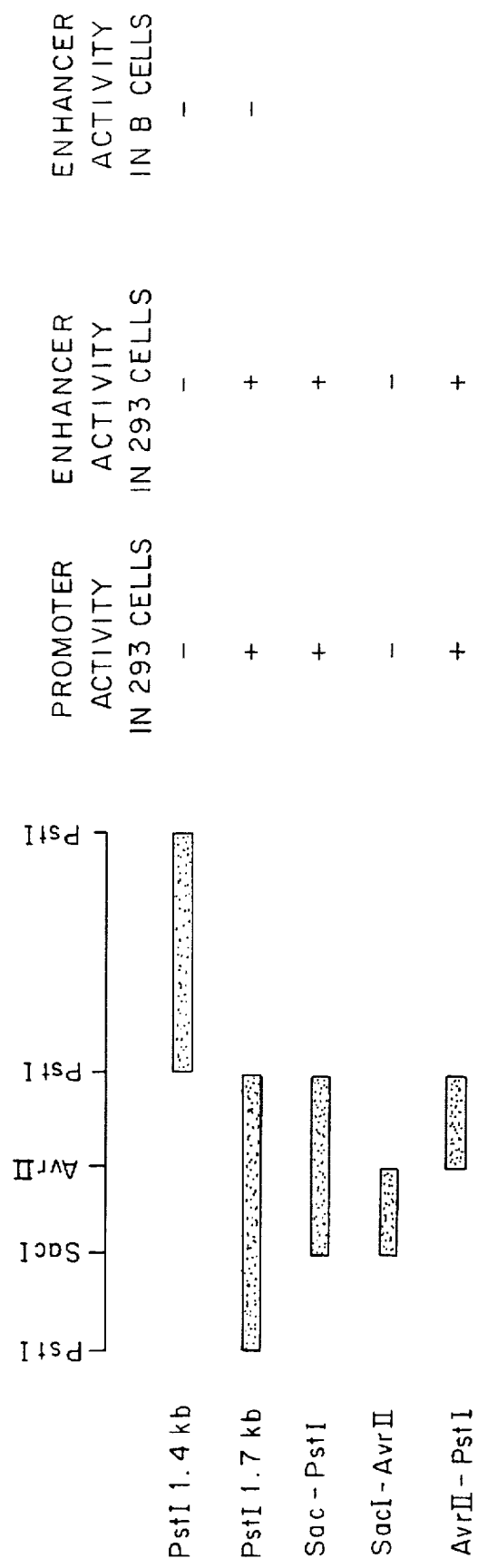
FIG. 2 shows schematically the promoter and enhancer activities of DH-sites II and III of the first intron of the p55 TNF-R gene; the various constructs containing different DH-sites are shown on the left hand side; and the promoter and enhancer activities of each of the constructs are shown on the right hand side, all as described in Example 1.

The tested fragments were: a 1.4 kb PstI fragment containing DH-site III; a 1.7 kb PstI fragment containing DH-sites IIa and IIb; a 973 bp SacI-PstI fragment containing DH-sites IIa and IIb; a 417 bp SacI-AvrII fragment containing DH-site IIa; and a 556 bp AvrII-PstI fragment containing DH-site IIb (for all fragments and DH-sites, see FIGS. 1 and 2). For transfection of the cells, adherent 293 cells were transfected by the standard CaPO$_4$ method, and B cells (Ramos, Raji and Daudi) were transfected by the standard DEAE-Dextran method (47). Luciferase activity in the transfected cells was measured by standard procedures (47).

The results of the above analysis are shown in FIG. 2 which is a schematic representation of the various fragments carrying the DH-sites as noted above (left hand side, depicted as filled blocks, see also FIG. 1) and the promoter activity in 293 cells, enhancer activity in 293 cells and enhancer activity in B cells of each of these fragments (right hand side). The promoter and enhancer activities of the fragments are indicated by symbols having the following meanings: −=no activity, +=positive activity and blank spaces=not done.

Thus, from the results shown in FIG. 2, it is apparent that as regards the 293 cells a 1.7 kb genomic PstI fragment containing site II has enhancer activity on the p55 TNF-R promoter as well as promoter activity of its own in 293 cells. Both promoter and enhancer activities were orientation-independent (data not shown). Deletion constructs, i.e., the above noted SacI-PstI, SacI-AvrII and AvrII-PstI fragments, all included in the 1.7 kb PstI fragment, showed that both enhancer and promoter activities were located in a 556 bp AvrII-PstI fragment. This fragment includes DH-site IIb, but excludes site IIa (FIG. 1). The 1.4 kb PstI fragment which includes only the DH-site III had neither promoter nor enhancer activities. Further, since we presumed that the enhancer fragment was responsible for the lack of p55 TNF-R expression in certain B cell lines, we also investigated the enhancer activity in Ramos, Raji and Daudi cells. As is also apparent from FIG. 2, the enhancer activity of the 1.7 kb PstI fragment (active in 293 cells) was, however, absent in these B cell lines, demonstrating its tissue-specificity in accordance with the observed pattern of DH-site II (see Table 1).

(iii) Sequence Analysis of DH-sites IIa and IIb

In order to find out whether the observed promoter and enhancer activities of the 1.7 kb PstI fragment containing DH-sites IIa and IIb, were caused by known transcription-factor binding sites, we sequenced a 973 bp SacI-PstI fragment which contains both sites IIa and IIb (see FIGS. 1 and 2 ). This SacI-PstI fragment was subcloned by standard procedures into a Bluescript™ (Stratagene) vector and sequenced by the standard method of 'primer walking'. The sequence of this fragment is shown in FIG. 3 (SEQ ID NO:1). This sequence was then analyzed for the presence of transcription factor-binding motifs using the GCG computer program (47). In the sequence of FIG. 3 there are shown: the restriction enzyme sites SacI, AvrII and PstI; the region containing the DH-sites IIa and IIb, denoted by italics (i.e., from nucleotide no. 1–160 of FIG. 3 (and of SEQ ID NO:1) is site IIa and from nucleotide no. 417–613 of FIG. 3 (and of SEQ ID NO:1) is site IIb); and the transcription factor-binding motifs, denoted by underlined parts of the sequence. The various indicated transcription factor-binding motifs shown in FIG. 3 are as follows: S1 HS (39), Sp1 (48), EARLY-SEQ1 (49), HTLV-pA-BS.1 (50), Octamer (51), Kr/bcd (52), AP-1 (53), Heptamer (54), JCV (40), SV40.13 (55), NFkB (56), PR-uteroglobin (57).

Thus, as is apparent from FIG. 3, analysis of the sequence of the SacI-PstI fragment for the presence of transcription factor-binding sites revealed the presence of several sites for B-cell specific transcription factors (octamer, heptamer) within the region of DH-site IIa. The region of DH-site IIb, however, showed only an SP-1 site and several GC-rich motifs (JCV). This indicated that either site IIb contains binding sites for unknown B-cell-specific transcription factors or that it interacts in vivo with site IIa in order to generate its specificity.

As is set forth in Examples 2, 3 and 4 below, the promoter/enhancer element of the first intron of the p55 TNF-R gene may also be used (i) as a substrate to identify factors binding to this promoter/enhancer region; (ii) for the purification of transcription factors binding to the promoter/enhancer region; and (iii) as a substrate for the modulation of promoter/enhancer activity by specific sequence regions. Moreover, in view of the apparent tissue-specificity of this intronic promoter/enhancer region, the above uses (i)–(iii) can be extended to isolate and purify those factors that act in a tissue-specific manner, and to achieve tissue-specific modulation.

Example 2

Initial Steps Towards Identification of Factors Binding to the Promoter Region A simple way to identify factors which bind to a given sequence is the electrophoretic mobility shift assay (EMSA), which was employed in the procedure disclosed in U.S. Ser. No. 08/178,564, abandoned, this procedure being incorporated herein by reference. Briefly, by this procedure, the 175 bp fragment BglII-EcoRI was labeled at the 5' end by a fill-in reaction using Klenow Polymerase and (32) P-dCTP. 10,000 cpm of labeled fragment were incubated in with 5 µg total protein of HeLa cell nuclear extract under varying buffer conditions and separated on a 3.5% native acrylamide gel. The experiments demonstrated the following:

(1) several minor and one major band were observed, corresponding to potential transcription factors binding to the BglII-EcoRI fragment;

(2) incubation of the nuclear extract with an excess of unlabeled BglII-EcoRI fragment completely abolished binding, indicating that the observed interactions are specific;

(3) addition of non-specific competitor DNA (salmon sperm DNA) reduced background, but did not abolish the appearance of the major band;

(4) salt concentrations of up to 250 mM of $Na^+$ and $K^+$ left binding unaffected, again demonstrating the specific nature of this interaction, as non-specific binding is often reduced or abolished upon an increase in salt concentration;

(5) increase in $Mg^{++}$ concentration up to 10 mM decreased but did not abolish binding to all observed complexes;

(6) identical binding patterns were observed at 20° C. and at 0° C.;

(7) no binding could be observed when cytoplasmic extracts of HeLa cells were used. This demonstrates once more the specific nature of the binding, since active transcription factors are expected to be localized to the nucleus of the cells.

Taken together, the data suggested that at least one factor interacts specifically with the region essential for promoter activity of the p55 TNF receptor upstream gene sequence. Likewise, the 1.7 kb PstI, 973 bp SacI-PstI and 0.6 kb AvrII-PstI fragments having the intron promoter of the present invention (see Example 1) may be used to identify factors binding to this promoter region.

Example 3

Purification of Transcription Factors Binding to the Promoter Region

Functional transcription factor-binding motifs in the promoter region can be identified by step-wise deletion of nucleic acid sequence from the 3' and/or 5' end of the promoter by conventional means (Erase-a-Base kit, Promega Corp.). The deleted promoter fragments are then tested for activity. Likewise, internal sequences can be deleted or changed by in vitro mutagenesis or linker scanning (37). Motifs that bind activating transcription factors are revealed by a loss of promoter activity when deleted or mutated. Conversely, motifs that bind transcription factors which suppress promoter activity are identified by mutated or deleted promoter fragments which have increased activity, compared to the wild-type promoter. A detailed analysis of these motifs is then carried out by chemical synthesis of oligonucleotides with the sequence of the original motif, and mutated forms of it. These oligonucleotides are linked to the promoter fragments lacking the corresponding motifs, and the resulting construct is tested for promoter activity. If the original activity is restored, the motif can be regarded as functionally unchanged, i.e., those mutations that were introduced into the motif, do not interfere with its function. On the other hand, if less promoter activity is observed with a mutated motif, it can be concluded that the nucleotides which were changed compared to the wild-type motif, are essential for its function.

Once a transcription factor-binding motif has been identified, the corresponding transcription factor is isolated. For this purpose, extracts from several sources are screened for high expression of that transcription factor. The amount of transcription factor present can be measured by gel shift assays, using the above described oligonucleotides containing the sequence of the functional motif as 5l'-end-labeled, ds-DNA probes.

Having identified an abundant source of the transcription factor, the conditions that are required for optimum binding can be defined. Different chemical parameters, such as pH, presence of various mono- and divalent cations, salt concentration and the presence of reducing agents, e.g. DTT or mercaptoethanol are adjusted to achieve this goal.

After establishing optimal binding conditions for the transcription factor, purification is carried out by conventional means, e.g., by salt precipitation, phosphocellulose and/or DEAE chromatography. An enriched precipitation of the transcription factor is then purified further on a DNA affinity column, in which the oligonucleotide containing the corresponding motif is bound to an insoluble matrix, and the transcription factor-containing solution is passed over the column under conditions optimal for binding. After washing off contaminants, the purified transcription factor is eluted by conditions which do not allow DNA binding, e.g., pH shift, changed salt concentration, or chelation of divalent salts necessary for DNA binding (usually $Zn^{++}$)

Having purified the transcription factor allows the application of "reverse genetics" on that molecule: protein sequencing, cDNA cloning using degenerated oligonucleotides corresponding to protein sequence and finally, cloning of the gene encoding the transcription factor by screening genomic libraries using the cDNA as a probe.

Having all these tools: genomic clones, cDNA and purified transcription factors, allows to define ways to regulate the activity of the transcription factor by one of the following means: (1) influencing its promoter; (2) influencing its binding to the target in the p55 TNF-R gene promoter region of the first intron; or (3) modulating its activity.

A detailed procedure for (1) is given in Example 4. Methods (2) and (3) can be achieved by screening a large number of drugs for interference with the function of this transcription factor.

Example 4

Modulation of Promoter Activity by Specific Sequence Regions

The activity of a promoter can be regulated by scavenging transcription factors which are in short supply. This can be done by expressing multiple copies of the corresponding motifs t o which the transcription factors bind. This mechanism has recently been demonstrated by Pai et al. (41), who expressed and amplified the negative promoter domain of the c-myc promoter in the hamster CHO cell line. Following that, the authors observed increased expression of hamster c-myc and the corresponding changes in cell growth and morphology induced by myc protein. Much in the same way, it is possible to amplify promoter regions which activate and enhance promoter activity, and causing a decrease in the expression of the corresponding protein by proceeding in this way.

For the p55 TNF-R promoter region of the first intron, either the whole promoter region or parts of it which have been identified as negative or positive regulatory domains, can be excised from the promoter sequence by restriction digest or exonuclease deletion of irrelevant sequences. The fragments obtained are then linked to a vector that allows gene amplification, and transfected into a cell line, e.g., CHO cells, which allows selection for amplified vector sequences. After selection and amplification, the clones of CHO cells obtained are checked for p55 TNF-R gene expression on the mRNA and protein level. In addition, the function of the receptors is checked by cytotoxicity assay with TNF or with TNF mimicking antibodies which cross-react with the hamster receptor (e.g., the mouse anti-p55 TNF-R antibodies).

Having established promoter regions which, upon amplification in this system, modulate the activity of the p55 receptor, these same regions are introduced into cells which do not allow selection for amplified gene products in two ways:

1) coexpression of promoter regions linked to a vector which contains a viral origin of replication (e.g., SV40 or EBNA), with a vector which expresses T antigen (of SV40), or EBNA antigen. This allows the replication of high numbers of episomal copies of the introduced promoter fragment in the nucleus of the target cell and thus mimics the effect of DNA amplification of integrated sequences. 2) chemical synthesis of a ds oligonucleotide comprising the promoter domain and application of sufficient amounts of that oligonucleotide to cells makes it likewise possible to scavenge the corresponding transcription factors and thus influence promoter activity. The chemistry of the oligonucleotides has to be changed in order to (a) make the oligonucleotide more lipophilic, so that it can pass the cytoplasmic membrane, and (b) enhance its stability in order to minimize degradation. This is done by conventional means, e.g., by using phosphothioate-coupled oligonucleotides.

The transitional term "comprising" or "comprises", when used in the present claims in relation to DNA sequences, is intended to be open insofar as what else may be present in the molecule in addition to the core sequence. Thus, DNA comprising a specified core sequence encompasses the specified sequence as well as anything else flanking that sequence. Such language does not comprehend insertions, deletions or substitutions within the specified sequence unless such insertions, deletions or substitutions are otherwise specified in the claim.

The term "consisting essentially of", when used in the present claims in relation to DNA sequences, is intended to have the same meaning established by the courts for such language when used in claims with respect to compositions. Thus, a claim drawn to a DNA molecule consisting essentially of a specified sequence includes any nucleotide sequence, or other moieties, flanking the specified sequence as long as the flanking material does not affect the basic and novel characteristics of the claimed core sequence. As with "comprising", such language does not comprehend insertions, deletions or substitutions within the specified sequence unless such insertions, deletions or substitutions are otherwise specified in the claim. It is specifically intended that such "consisting essentially of" language exclude a sequence which comprises the entire genome or any isolated fragments of the entire genome which may have been known to the prior art but in which the claimed core sequence was not considered to be an essential portion and in which the basic and novel characteristics of the claimed core sequence were totally unknown. It is intended to include entire expression vectors as well as an entire recombinant genome in which such a core sequence has been inserted for a specified purpose.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Tracey, J. T. et al. (1987) Nature, 330:662–664.
2. Piquet, P. F. et al. (1987) J. Exp. Med., 166:1280–89.
3. Beutler, B. and Cerami, C. (1987) NEJM, 316:379 385.
4. Hohmann, H.-P. et al. (1989) J. Biol. Chem., 264:14927–14934.
5. Engelmann, H. et al. (1990) J. Biol. Chem., 265:1531–1536.
6. Brockhaus, M. et al. (1990) Proc. Natl. Acad. Sci. USA, 87: 3127–3131.
7. Loetscher, H. et al. (1990) Cell, 61:351–359.
8. Schall, T. J. et al (1990) Cell, 61:361–370.
9. Nophar, Y. et al. (1990) EMBO J., 2:3269–3278.
10. Smith, C. A. et al. (1990) Science, 248:1019–1023
11. Heller, R. A. et al. (1990) Proc. Natl. Acad. Sci. USA, 87: 6151–6155.
12. Aggarwal, B. B. et al. (1985) Nature, 318:665 667.
13. Israel, S. et al. (1986) Immunol. Lett., 12:217 224.
14. Tsujimoto, M. et al. (1986) Biochem. Biophys. Res. Commun., 137: 1094–1100.
15. Ruggiero, V. J. et al. (1986) J. Immunol., 136:2445.
16. Holtmann, H. and D. Wallach (1987) J. Immunol., 132:1161–1167.
17. Ding, A. H. et al. (1989) J. Biol. Chem., 264:3924.
18. Porteu, F. and Nathan, C. (1990) J. Exp. Med., 17:599 607.
19. Porteu, F. et al. (1991) J. Biol. Chem., 266:18846.
20. Ware, C. F. et al. (1991) J. Immunol., 147:4229.
21. Erikstein, B. K. et al. (1991) Eur. J. Immunol., 21: 1033.
22. Winzen, R. et al. (1992) J. Immunol., 148:3454.
23. Espevik, T. et al. (1990) J. Exp. Med., 171:415 426.
24. Engelmann, H. et al. (1990) J. Biol. Chem., 265: 14497–14504.
25. Thoma, B. et al. (1990) J. Exp. Med., 172:1019–1023.
26. Tartaglia, L. A. et al. (1991) Proc. Natl. Acad. Sci. USA, 88:9292–6
27. Gehr, G. et al. (1992) J. Immunol., 149:911
28. Heller, R. A. et al. (1992) Cell, 70:47.
29. Brakebusch, C. et al. (1992) EMBO J., 11 :943–950.
30. Vandenabeele, P. et al. (1992)J. Exp. Med., 176:1015.
31. Gey, G. O. et al. (1952) Cancer Res., 12:254 265.
32. Littlefield, J. W. (1964) Nature, 203:1142.
33. Sundstrom, C. and Nillson, K. (1976) Int. J. Cancer, 17: 565–577.
34. Derre, J. et al. (1991) Hum. Genet., 87:231–233.
35. Benech, P. et al. (1987) Mol. Cell. Biol., 7:4498–4504.
36. Sanger, F. et al. (1977) Proc. Natl. Acad. Sci. USA, 74:5463–5467.
37. Sambrook, J. et al. (1989) *Molecular Cloning: A Laboratory Manual*. Cold Spring Harbor Laboratory Press, Cold Spring Harbor, N.Y.
38. Fuchs, P. et al. (1992) Genomics, 13:219 224.
39. Johnson, A. C. et al. (1988) Mol. Cell. Biol., 8:4174–4184.
40. Martin, J. D. et al. (1985) J. Virol., 53:306–311.
41. Pai et al. (1992) J. Biol. Chem., 267:12428–31.
42. Felsenfeld, G. (1992) Nature 355:219–224.
43. Kim, J. S. and Kemper, B. (1991) Biochemistry 30:10287–10294.
44. Wu, C. (1980) Nature 286:854–860.
45. Wu, C. (1984) Nature 309:229–234.
46. Kemper, O. and Wallach, D. (1993) Gene 134:209–216
47. Ausubel, F. M., Brent, R., Kingston, R. E., Moore, D., Seidman, J. G., Smith, J. A. and Struhl, K. (1987) Current protocols in Molecular Biology. Current protocols, Greene and Wiley Inc, New York.
48. Dynan, W. S., Sazer, S., Tjian, R. and Schimke, R. T. (1986)Nature 319:246–248.
49. Fromm, M. and Berg, P., (1982) J. Mol. Appl. Genet. I :457 481.
50. Levinger, L. F. and Lautenberger, J. A. (1987) Eur. J. Biochem. 166:519 526.
51. Sturm, R., Baumruker, T., Franza, B. R. Jr. and Herr, W. (1987) Genes Dev. 1:1147–1160.
52. Stanojovec, D., Small, S. and Levint M. (1991) Science 254:1385–1387.
53. Lee, W., Mitchell, P. and Tjian, R. (1987) Cell 49:741–752.
54. Landolfi, N. F., Yin, X. M., Capra, J. D. and Tucker, P. W. (1988) Nucleic Acids Res. 16:5503–5514.
55. Pfeifer, K., Arcangioli, B. and Guarente, L. (1987) Cell 49:9–18.
56. Leung, K. and Nabel, G. J. (1988) Nature 333:776–778.
57. Bailly, A., Le Page, C., Rauch, M. and Milgrom, B. (1986) EMBO J. 5:3235–3241.
58. Koizumi, M. et al. (1993) Biol. Pharm. Bull (Japan) 16879 83.
59. Crisell, P. et al. (1993) Nucleic Acids Res. 21:5251–5.
60. Barinaga, M. (1993) Science 262: 1512–4.
61. Cantor, G. H. et al. (1993) Proc. Natl. Acad. Sci USA 90: 10932–6.
62. Shimayama, T. et al. (1993) Nucleic Acids Symp. Ser. 29:177–8.
63. Joseph'S. and Burke, J. M. (1993) J. Biol. Chem. 268:24515–8.
64. Chen, C. J. et al. (1992) Ann N.Y. Acad. Sci. 660:271–3.
65. Shore, S. K. et al. (1993) Oncogene 8:3183–8.
66. Zhao, J. J. and Pick, L. (1993) Nature 365:448–51.
67. Deverelux, J. et al. (1984) Nucleic Acid Res. 12:387 95.

We claim:

1. A DNA molecule comprising the endogenous first intron-located p55 TNF-R gene promoter/enhancer sequence, provided that said molecule contains no more of the p55 TNF-R gene than the first intron thereof.

2. A DNA molecule in accordance with claim 1, wherein said molecule contains no more of the p55 TNF-R gene than the 1.7 kb PstI fragment of the 3' region of the first intron of the human p55 TNF-R gene.

3. A DNA molecule in accordance with claim 2, wherein said molecule contains no more of the p55 TNF-R gene than the 973 bp SacI-PstI fragment contained in said 1.7 kb PstI fragment, said SacI-PstI fragment having the sequence of SEQ ID NO:1.

4. A DNA molecule in accordance with claim 2, wherein said molecule contains no more of the p55 TNF-R gene than the 556 bp AurII-PstI fragment contained in said SacI-PstI fragment.

5. A DNA molecule consisting of the endogenous first intron-located p55 TNF-R gene promoter/enhancer sequence.

6. In a recombinant DNA molecule comprising a gene to be expressed, other than the p55 TNF-R gene, and a promoter sequence operatively associated therewith, which promoter sequence functions to promote the expression of said gene, the improvement wherein said promoter sequence comprises the endogenous first intron-located p55 TNF-R gene promoter/enhancer sequence.

7. A DNA molecule in accordance with claim 6, wherein said promoter sequence comprises the 556 bp AurII-PstI fragment contained in the SacI-PstI fragment of SEQ ID NO:1.

8. A DNA molecule in accordance with claim 6, wherein said promoter sequence comprises the 973 bp SacI-PstI fragment having the the sequence of SEQ ID NO:1.

9. A DNA molecule in accordance with claim 8, wherein said promoter sequence comprises the 1.7 kb PstI fragment of the 3' region of the first intron of the human p55 TNF-R gene.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 973 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GAGCTCACGG | AATGGGTTTA | GCTGTTGGAG | ACTTGTTGAA | CTGGGAGGAG | GAGCTGGGGC | 60 |
| GGGGCCTCAG | CTAAAGGCCG | CTGAGGGGCT | AGGAGGAGCC | AAGTGGCCCT | CAGGGAAGGG | 120 |
| AGGGCACAGA | CCTGATGGGC | GGAAGCAGGG | TCGAGGGAGA | CTTCCCTTCG | GATGGAATGG | 180 |
| GGAGAGGGAG | GCATTTCCCG | GAACATGTGG | GCCAAGGTGG | GACAAGGGTC | TGTGGCCTGG | 240 |
| CTCTTTGCAT | GGGGAGGGGA | TGGATGGGGG | TTGAGTGGGG | ATGGGGAAGG | AGGGACTTGG | 300 |
| CCATAGGAAG | AAGGGATTAG | ATGGAGTCCC | ACTTGCATGC | AGGCTGGTGC | CTTCTGCCTT | 360 |
| TCTGCTGACT | CATGACCCTT | GAGGAGCTGG | GGAAGCTGCT | AGTTCCCTCT | CCCCTCCCTA | 420 |
| GGTCTCCCTC | CCTCTGGCCT | GAGTCACTGG | GGCGGAGTTG | CTGGGAAAAG | ATTTCCCTTT | 480 |
| CCCGGATCTG | ACTTAACCCC | CAGAGTGCTG | GAAAGAGAAG | GGAACACGTG | GCCTGAGAAA | 540 |
| GCCTCTCTCC | CTCCCTCCCT | CCAGGGAGGC | TCATCCCCCA | CTGGCCAGAG | GTCCCTGAAA | 600 |
| ATGCTCCCCT | TTAAGGCTGT | CTGGGGCTGG | GCGTCCCCCA | GTTCTTCATC | ATGACTCTGC | 660 |
| CTCAAGCCCC | CTGGATGGGA | TTCAAAGTAC | CAGTGACCTT | AGGTGCTCCA | GTGGCTTCTT | 720 |
| CGGGGAAAGG | AACCACACTT | TCAGGACTGG | AAGTCTTCCC | TACACACCCA | ACCTTCCTGT | 780 |
| TGCCTGGAAG | CCCCAGTCCT | GTTCTCAGCA | GAGGTGGCAC | GGTGTTGGCT | GGTGCGGGCA | 840 |
| GGGGAAGGTT | GTTGTCCTCT | GAGCAGGGGC | ACACGCCTCC | ACCTGCGGGG | GCTGCTGTTG | 900 |
| TGTTTCTGTG | TGTGGCTTCC | CCTGTTTGCG | GCTGAGGCTT | GAACTTCCGG | GCCTGCACAG | 960 |
| CTTACAGCTG | CAG | | | | | 973 |

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | |
|---|---|---|
| CAATTCAGAA | TGCTTAGCTT | T | 21 |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GATCAGTAAA TTCCCAAGAA AGA 23